United States Patent [19]

Irikura et al.

[11] Patent Number: 4,472,579
[45] Date of Patent: Sep. 18, 1984

[54] PROCESS FOR THE PREPARATION OF QUINOLINE CARBOXYLIC ACID DERIVATIVES

[75] Inventors: Tsutomu Irikura, Tokyo; Toshie Shiba; Hiroshi Matsukubo, both of Nagano, all of Japan

[73] Assignee: Kyorin Seiyaku Kabushiki Kaisha, Japan

[21] Appl. No.: 298,333

[22] Filed: Aug. 31, 1981

[30] Foreign Application Priority Data

Sep. 5, 1980 [JP] Japan .................................. 55-123024

[51] Int. Cl.³ .......................................... C07D 401/04
[52] U.S. Cl. .................................. 544/363; 544/404; 546/156
[58] Field of Search .......................................... 544/363

[56] References Cited

U.S. PATENT DOCUMENTS

| | | | |
|---|---|---|---|
| 2,504,875 | 4/1950 | Price et al. | 546/153 |
| 4,017,622 | 4/1977 | Minami et al. | 544/362 |
| 4,146,719 | 3/1979 | Irikura | 544/363 |
| 4,292,317 | 9/1981 | Pesson | 544/363 |

*Primary Examiner*—Donald G. Daus
*Assistant Examiner*—S. A. Gibson

*Attorney, Agent, or Firm*—Toren, McGeady and Stanger

[57] ABSTRACT

Process for the preparation of useful antimicorbial agents, 1-substituted-6-fluoro-7-(1-piperazinyl or 4-substituted-1-piperazinyl)-4-oxo-1,4-dihydroquinoline-3-carboxylic acids having the chemical structure [IV],

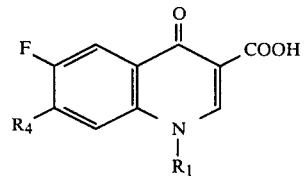

wherein
$R_1$ is ethyl or vinyl group, and
$R_4$ is

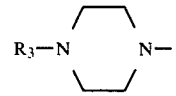

($R_3$ is hydrogen atom or lower alkyl group).

1 Claim, No Drawings

PROCESS FOR THE PREPARATION OF QUINOLINE CARBOXYLIC ACID DERIVATIVES

BACKGROUND OF THE INVENTION

1. Field of the Invention:

This invention relates to a process for preparation of valuable antimicrobial agents. More particularly, it relates to the process for the preparation of quinoline carboxylic acid derivatives.

2. Description of the Prior Art:

Previously, the present inventors made clear that 1-ethyl-6-fluoro-7-(1-piperazinyl)-4-oxo-1,4-dihydroquinoline-3-carboxylic acid has more potent antimicrobial activities than the known antimicrobial agents, and reported the process for the preparation of the above compound, simultaneously (Japanese Laid-Open Patent Application No. Sho 53-141286). Also, the preparations of 1-ethyl-6-fluoro-7-(4-methyl-1-piperazinyl)-4-oxo-1,4-dihydroquinoline-3-carboxylic acid and the related compounds were reported by the present inventors (Japanese Laid-Open Patent Application No. Sho 54-138582, No. Sho 55-40656 and No. Sho 55-47658). Further, many substituted quinoline carboxylic acids and their preparation have been also stated by Pesson (France) in Japanese Laid-Open Patent Application No. Sho 54-66686.

In the above prior arts, the antimicrobial agents [IV] are prepared by the reaction of the corresponding carboxylic acid [V],

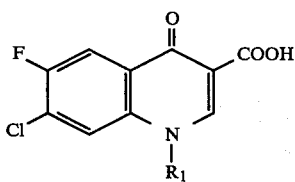

wherein $R_1$ is defined as above, with the compound [II]. In this method, the purity of the starting material [V] and the reaction condition exert an awful influence upon the yield of the purified product [IV].

Namely, the purification of the material [V] is difficult because of its slight solubility in various kinds of solvents, so it is hard to obtain pure material [V] in industrial scale. Furthermore, even if the purified material [V] is used in the reaction with the compound [II], a following compound [VI],

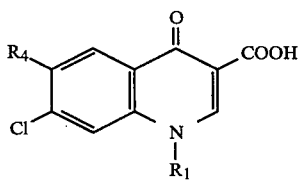

wherein $R_1$ and $R_4$ are defined as above, is produced as a by-product. The formation of the by-product causes lowering of the yield of the purified product [IV].

SUMMARY OF THE INVENTION

This invention relates to the process for the preparation of useful antimicrobial agents, 1-substituted-6-fluoro-7-(1-piperazinyl or 4-substituted-1-piperazinyl)-4-oxo-1,4-dihydroquinoline-3-carboxylic acids having the chemical structure [IV],

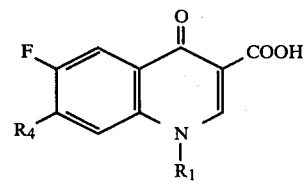

wherein
$R_1$ is ethyl or vinyl group, and
$R_4$ is

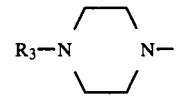

($R_3$ is hydrogen atom or lower alkyl group), and more particularly, relates to the process of industrial manufacture of antimicrobial agents represented by the formula [IV] having high purity. The intermediate substances, 1-substituted-6-fluoro-7-(1-piperazinyl or 4-substituted-1-piperazinyl)-4-oxo-1,4-dihydroquinoline-3-carboxylic acid esters [III] are prepared by the reaction of the corresponding 7-halo-4-oxo-1,4-dihydroquinoline-3-carboxylic acid esters [I],

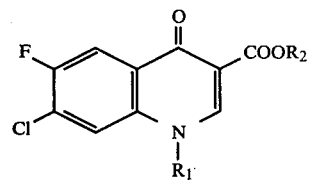

wherein $R_1$ is defined as above, and $R_2$ is lower alkyl group, with piperazine derivative [II]

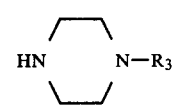

wherein $R_3$ is defined as above. And then, desired antimicrobial agents [IV] are prepared by hydrolysis of the intermediate compounds represented by the formula [III],

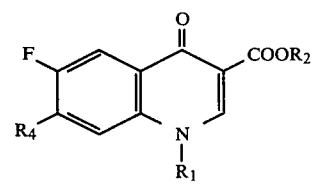

wherein $R_1$, $R_2$ and $R_4$ are defined as above.

The present invention was accomplished as a result of studies for industrial preparation of the antimicrobial agent having a high purity. The application of 6-fluoro-4-oxo-1,4-dihydroquinoline-3-carboxylic acid esters as a starting material is the main point of the present invention.

In the present invention, we found, surprisingly, the above-mentioned by-product was not produced as a result of confirmation by high-speed liquid chromatography. Therefore, the product [IV] is obtained in a high yield and can be easily purified. Moreover, the intermediate substance [III] is soluble in many solvent and so easily purified. The present invention has marked characteristics on these points when compared with the prior arts.

DETAILED DESCRIPTION OF THE INVENTION

In the present invention, a mixture of the starting material [I] (1 mol), organic base, and piperazine derivative [II] (2-4 mol) is heated in a range of 90°-150° C., preferably 110°-120° C., in the presence or absence of non-polar solvent. The heating time is varied depending on the reaction temperature and, for example, the reaction at 110° C. is completed within 5 hrs. Organic bases such as, for example, pyridine, picoline, triethylamine or the like, may be used in the reaction. These organic bases may serve as the reaction solvent, and volume of the base may be decreased when a non-polar solvent such as, for example, benzene, toluene or the like, is used.

In the hydrolysis reaction using an acid, it is desirable that the intermediate substance [III] is refluxed in a mixture of mineral acid such as hydrochloric acid, and organic acid such as acetic acid. In the hydrolysis reaction using an alkali, the intermediate substance [III] is heated in a diluted sodium hydroxide solution in a range of 50°-100° C., preferably at 90°-95° C. The hydrolysis reaction by the acid needs several hours, but the reaction using the alkali is accomplished in a few minutes.

EXPERIMENT 1

Antibacterial Activity

The antibacterial activities of the compounds of this invention were assayed by the standard agar dilution streak method against Gram-positive and Gram-negative bacteria [Chemothrapy, 22, 1126 (1974)]. The result was shown in Table 1 together with a known agent, nalidixic acid. The compounds of Examples 1, 6, 8 and 9 in the present invention were more active than nalidixic acid against Gram-positive and Gram-negative bacteria.

DESCRIPTION OF PREFERRED EMBODIMENTS

The following examples serve to illustrate and explain the present invention, but the present invention should not be limited thereto.

EXAMPLE 1

Anhydrous piperazine (19.5 g) and 1-ethyl-6-fluoro-7-chloro-4-oxo-1,4-dihydroquinoline-3-carboxylic acid ethyl ester (16.8 g) were added to 34 ml of pyridine, and the mixture was refluxed with stirring for 5 hrs. The reaction mixture was concentrated under reduced pressure and the residue was dissolved in 100 ml of chloroform. The chloroform layer was washed with water for three times.

After the chloroform layer was dried over anhydrous magnesium sulfate, the chloroform was evaporated under reduced pressure and the residue was dissolved with heating in benzene. After filtered, the benzene layer was cooled. The precipitated crystals were recrystallized from a mixture of methylene chloride (50 ml) and benzene (100 ml) to give 17.3 g (88% yield) of 1-ethyl-6-fluoro-7-(1-piperazinyl)-4-oxo-1,4-dihydroquinoline-3-carboxylic acid ethyl ester. mp: 178.5°-180° C.

|  | C | H | N |
|---|---|---|---|
| Anal. Calcd. for $C_{18}H_{22}FN_3O_3$: | 62.31 | 6.22 | 12.03 |
| Found: | 62.23 | 6.38 | 12.10 |

MS (m/e): M+ 347 (Calcd. 347).

IR (KBr): 3320 cm$^{-1}$ ($\omega$, piperazine nuclear N—H), 1729 cm$^{-1}$ (s, C═O of ester), 1623 cm$^{-1}$ (s, C═O in ring).

NMR ($\delta$): 1.30–1.62 ppm (m, CH$_3$.CH$_2$—), 2.95–3.28 ppm (m, —CH$_2$CH$_2$—), 4.00–4.48 ppm (m, CH$_3$.CH$_2$—), 6.60–6.74, 7.83–8.03, and 8.29 ppm (m and s,

To a hot (90° C.) solution of 6% aqueous sodium hydroxide (40 ml) was added the above ester (5 g). After kept at the same temperature for 5 minutes, the reaction mixture was cooled in the water. The reaction mixture was adjusted to pH 7.5 with diluted hydrochlo-

TABLE 1

Antibacterial Activity (Minimum inhibitory concentration) (μg/ml)

| Organisms | Gram | The compound of | | | | NA |
| | | Ex. 1 | Ex. 6 | Ex. 8 | Ex. 9 | |
|---|---|---|---|---|---|---|
| *Bacillus subtilis* PCI219 | + | 0.39 | 0.10 | 0.39 | 0.39 | 6.25 |
| *Staphyloccocus aureus* 209P | + | 0.78 | 0.39 | 3.13 | 1.56 | 50 |
| *S. aureus* ATCC14775 | + | 3.13 | 0.39 | 6.25 | 3.13 | >100 |
| *Streptococcus pyogenes* IID692 | + | 1.56 | 6.25 | 12.5 | 12.5 | >100 |
| *Diplococcus pneumoniae* IID552 | + | 3.13 | 3.13 | — | — | >100 |
| *Escherichia coli* NIHJ JC-2 | — | 0.10 | 0.10 | 0.10 | <0.10 | 3.13 |
| *Proteus vulgaris* IFO3167 | — | 0.10 | 0.10 | 0.20 | 0.20 | 3.13 |
| *Klebsiella pneumoniae* IFO3512 | — | 0.05 | 0.05 | 0.10 | <0.10 | 1.56 |
| *Pseudomonas aeruginosa* VI | — | 0.39 | 1.56 | 0.39 | 3.13 | 100 |
| *Pseudo. aeruginosa* IFO12689 | — | 1.56 | 3.13 | 1.56 | 3.13 | >100 |
| *Salmonella enteritidis* IID604 | — | 0.20 | 0.78 | 0.39 | 0.78 | 12.5 |
| *Shigella sonnei* IID969 | — | 0.10 | 0.10 | 0.20 | 0.20 | 1.56 |

NA: Nalidixic acid ric acid to obtain crystals. The crystals in 20 ml of methanol were stirred for a while, filtered off, dried, and recrystallized from a mixture of methylene chloride (25 ml) and ethanol (15 ml) to give 4.1 g (89% yield) of 1-ethyl-6-fluoro-7-(1-piperazinyl)-4-oxo-1,4-dihydroquinoline-3-carboxylic acid. mp: 221°–222° C.

EXAMPLE 2

A mixture of 18 ml of picoline, 10.3 g of anhydrous piperazine, and 8.9 g of 1-ethyl-6-fluoro-7-chloro-4-oxo-1,4-dihydroquinoline-3-carboxylic acid ethyl ester was refluxed with stirring for 5 hrs. The reaction mixture was concentrated under reduced pressure, and the residue was treated by the same manner described in Example 1 to give 8.2 g (79% yield) of 1-ethyl-6-fluoro-7-(1-piperazinyl)-4-oxo-1,4-dihydroquinoline-3-carboxylic acid ethyl ester. mp: 178°–180° C.

To a mixture of glacial acetic acid (170 ml) and concentrated hydrochloric acid (170 ml) was added 4.3 g of 1-ethyl-6-fluoro-7-(1-piperazinyl)-4-oxo-1,4-dihydroquinoline-3-carboxylic acid ethyl ester and the reaction mixture was concentrated under reduced pressure. The residue was dissolved in 10 ml of water and adjusted to pH 7.5 with diluted sodium hydroxide solution. The precipitated crystals were carried out by the same way in the Example 1 to give 3.3 g (84% yield) of 1-ethyl-6-fluoro-7-(1-piperazinyl)-4-oxo-1,4-dihydroquinoline-3-carboxylic acid. mp: 220.5°–222° C.

EXAMPLE 3

A mixture of 18 ml of triethylamine, 10.3 g of anhydrous piperazine, and 8.9 g of 1-ethyl-6-fluoro-7-chloro-4-oxo-1,4-dihydroquinoline-3-carboxylic acid ethyl ester was refluxed with stirring for 20 hrs. The reaction mixture was concentrated under reduced pressure, 30 ml of chloroform was added to the residue, and cooled at 0° C. to give crystals. The crystals were filtered to recover 2 g of 1-ethyl-6-fluoro-7-chloro-4-oxo-1,4-dihydroquinoline-3-carboxylic acid ethyl ester. The above filtrated solution was extracted with diluted hydrochloric acid, the hydrochloric acid layer was neutralized with diluted sodium hydroxide solution, and the neutralized solution was extracted with chloroform. The chloroform layer was washed with water and dried over anhydrous magnesium sulfate, the chloroform was evaporated under reduced pressure. The residue was treated by the same procedure in Example 1 to give 7.4 g (71% yield) of 1-ethyl-6-fluoro-7-(1-piperazinyl)-4-oxo-1,4-dihydroquinoline-3-carboxylic acid ethyl ester. mp: 178°–180° C.

The above product was hydrolyzed by operating as in Examples 1 and 2 to give the corresponding acid.

EXAMPLE 4

Anhydrous piperazine (10.3 g) and 1-ethyl-6-fluoro-7-chloro-4-oxo-1,4-dihydroquinoline-3-carboxylic acid ethyl ester were added to a mixture of pyridine (9 ml) and toluene (18 ml), and the mixture was refluxed with stirring for 5 hrs. The same procedure as described in Example 1 was followed to give 8.4 g (81% yield) of 1-ethyl-6-fluoro-7-(1-piperazinyl)-4-oxo-1,4-dihydroquinoline-3-carboxylic acid ethyl ester. mp: 178.5°–180° C.

The above ethyl ester was hydrolyzed by the same manner described in Examples 1 and 2 to give the corresponding acid.

EXAMPLE 5

A mixture of 1.7 g of anhydrous piperazine and 1.4 g of 1-ethyl-6-fluoro-7-chloro-4-oxo-1,4-dihydroquinoline-3-carboxylic acid methyl ester in 3 ml of pyridine was refluxed with stirring for 5 hrs. The reaction mixture was cooled to give crude crystals. The crude crystals were recrystallized from a mixture of methylene chloride and methanol to give 1.55 g (77.5% yield) of 1-ethyl-6-fluoro-7-(1-piperazinyl)-4-oxo-1,4-dihydroquinoline-3-carboxylic acid methyl ester. mp: 179°–181° C.

|  | C | H | N |
|---|---|---|---|
| Anal. Calcd. for C$_{17}$H$_{20}$FN$_3$O$_3$: | 60.87 | 6.19 | 12.22 |
| Found: | 61.25 | 6.05 | 12.60 |

MS (m/e): M+333 (Calcd. 333).
IR (KBr): 1712 cm$^{-1}$ (C=O in ester), 1631 cm$^{-1}$ (C=O in ring).
NMR (δ): 1.50 (t,—CH$_2$CH$_3$), 2.08 (s, NH), 2.90–3.35 (m,—CH$_2$CH$_2$—), 3.89 (s,—OCH$_3$), 4.18 (q,—CH$_2$CH$_3$), 6.67 (d, 8-H), 7.94 (d, 5H), 8.33 (s, 2-H).

The above methyl ester was hydrolyzed by the same way in the Example 1 to give 1.1 g (85.2% yield) of 1-ethyl-6-fluoro-7-(1-piperazinyl), 1,4-dihydroquinoline-3-carboxylic acid. mp: 220.5°–221.5° C.

EXAMPLE 6

To an 8 ml of pyridine were added 3.6 g of 1-methylpiperazine and 3.6 g of 1-ethyl-6-fluoro-7-chloro-4-oxo-1,4-dihydroquinoline-3-carboxylic acid ethyl ester, and the mixture was refluxed for 5 hrs.

The reaction mixture was concentrated under reduced pressure, 10 ml of water was added to the residue, and extracted with 10 ml of chloroform. The chloroform layer was dried, evaporated in vacuo, and the residue was recrystallized from a mixture of benzene and ethyl ether to give 3.1 g (72.1% yield) of 1-ethyl-6-fluoro-7-(4-methyl-1-piperazinyl)-4-oxo-1,4-dihydroquinoline-3-carboxylic acid ethyl ester. mp: 176°–179° C.

|  | C | H | N |
|---|---|---|---|
| Anal. Calcd. for C$_{19}$H$_{24}$FN$_3$O$_3$: | 63.28 | 6.73 | 11.40 |
| Found: | 63.14 | 6.69 | 11.63 |

MS (m/e): M+ 361 (Calcd. 361).
IR (KBr): 1723 cm$^{-1}$ (C=O in ester), 1620 cm$^{-1}$ (C=O in ring).
NMR (δ): 1.37, 1.48 (t,—CH$_2$CH$_3$×2), 2.34 (s, N—CH$_3$), 2.48–2.70

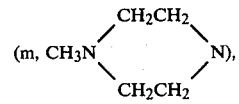

3.12–3.32

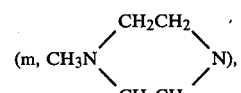

4.15, 4.32 (q, CH₂CH₃×2), 6.63 (d, 8-H), 7.87 (d, 5-H), 8.24 (s, 2-H).

The above ethyl ester was hydrolyzed by the same manner described in Example 1 to give 0.97 g (89.8% yield) of 1-ethyl-6-fluoro-7-(4-methyl-1-piperazinyl)-4-oxo-1,4-dihydroquinoline-3-carboxylic acid. mp: 271.0°–271.4° C.

EXAMPLE 7

A mixture of 8 ml of α-picoline, 4.8 g of 1-methylpiperazine, and 3.6 g of 1-ethyl-6-fluoro-7-chloro-4-oxo-1,4-dihydroquinoline-3-carboxylic acid ethyl ester was refluxed for 5 hrs. The reaction mixture was treated by operating as in Example 6 to give 2.8 g (64.8% yield) of 1-ethyl-6-fluoro-7-(4-methyl-1-piperazinyl)-4-oxo-1,4-dihydroquinoline-3-carboxylic acid ethyl ester. mp: 176°–177° C. The above ethyl ester was hydrolyzed by the same way in Example 1 to obtain the corresponding acid.

EXAMPLE 8

To a 120 ml of anhydrous dimethyl sulfoxide (DMSO), 6.32 g of 1-(2-chloroethyl)-6-fluoro-7-chloro-4-oxo-1,4-dihydroquinoline-3-carboxylic acid ethyl ester and 2.89 g of 1,8-diazabicyclo[5,4,0]-7-undecene were added and the mixture was heated at 84°–89° C. for 2 hrs. The reaction mixture was concentrated in vacuo and the residue was dissolved in chloroform. The chloroform layer was washed with water and dried. The residue obtained through evaporation of chloroform was recrystallized from ethyl ether to give 3.66 g (65.1% yield) of 1-vinyl-6-fluoro-7-chloro-4-oxo-1,4-dihydroquinoline-3-carboxylic acid ethyl ester. mp: 146°–149° C.

|  | C | H | N |
|---|---|---|---|
| Anal. Calcd. for C₁₄H₁₁ClFNO₃: | 56.72 | 3.66 | 4.85 |
| Found: | 56.87 | 3.75 | 4.74 |

MS (m/e): M⁺ 295 (Calcd. 295).
IR (KBr): 1723 cm⁻¹ (CO in ester), 1635 cm⁻¹ (C=C in vinyl), 1612 cm⁻¹ (C=O in ring).
NMR (δ): 1.40 (t,—CH₂CH₃), 4.36 (q,—CH₂CH₃), 5.61, 5.74 (dd,—CH=CH), 7.12 (dd,—CH=CH₂), 7.52 (d, 8-H), 8.05 (d, 5-H), 8.48 (s, 2-H)

Anhydrous piperazine (1.4 g) and 1.2 g of the above ethyl ester were added to a 3 ml of pyridine and the mixture was refluxed for 5 hrs. After cooled, the appeared crystals were filtered off, washed with ethanol, and recrystallized from a mixture of methylene chloride and benzene to give 1.0 g (71.4% yield) of 1-vinyl-6-fluoro-7-(1-piperazinyl)-4-oxo-1,4-dihydroquinoline-3-carboxylic acid ethyl ester. mp: 208°–210° C.

|  | C | H | N |
|---|---|---|---|
| Anal. Calcd. for C₁₈H₂₀FN₃O₃: | 62.25 | 5.78 | 12.02 |
| Found: | 62.60 | 5.84 | 12.17 |

IR (KBr) 3195 (NH), 1723 (C=O in ester), 1639 (C=C vinyl).
NMR (δ) 1.53 (t,—CH₂CH₃), 3.40–3.86

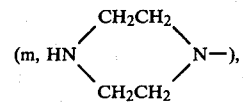

3.86–4.30

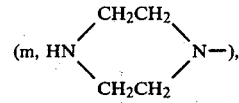

4.69 (q,—CH₂CH₃), 5.98–6.24 (m,—CH=CH₂), 7.37 (d, 8-H), 7.37–7.60 (m,—CH=CH₂), 8.28 (d, 5-H), 9.14 (s, 2-H).

The above ethyl ester was treated by the same manner described in Example 1 to give 1.8 g (92.4% yield) of 1-vinyl-6-fluoro-7-(1-piperazinyl)-4-oxo-1,4-dihydroquinoline-3-carboxylic acid. mp: 248.5°–251° C.

EXAMPLE 9

1-Methylpiperazine (1.6 g) and 1-vinyl-6-fluoro-7-chloro-4-oxo-1,4-dihydroquinoline-3-carboxylic acid ethyl ester (1.2 g) were added to a 3 ml of pyridine, and the mixture was refluxed for 5 hrs. The reaction mixture was concentrated in vacuo, water was added to the residue, and the mixture was adjusted to pH 4 with acetic acid. After filtering, the filtrate made alkali with sodium hydroxide solution. The crude crystals were recrystallized from a mixture of chloroform and benzene to give 1.0 g (68.5% yield) of 1-vinyl-6-fluoro-7-(4-methyl-1-piperazinyl)-4-oxo-1,4-dihydroquinoline-3-carboxylic acid ethyl ester. mp: 186.5°–187.5° C.

|  | C | H | N |
|---|---|---|---|
| Anal. Calcd. for C₁₉H₂₂FN₃O₃: | 63.27 | 6.25 | 11.59 |
| Found: | 63.50 | 6.17 | 11.69 |

IR (KBr): 1726 cm⁻¹ (C=O in ester), 1615 cm⁻¹ (C=O in ring).
NMR (δ): 1.39 (t,—CH₂CH₃), 2.38 (s, N—CH₃), 2.52–2.72

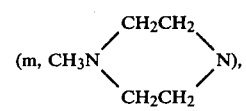

3.15–3.38

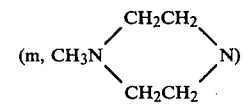

4.36 (q,—CH₂CH₃), 5.56 and 5.68 (dd, —Ch=CH₂) 6.64 (d, 8-H), 7.11 (dd, —Ch=CH₂), 7.84 (d, 5-H), 8.38 (s, 2-H).

The above ethyl ester (1.1 g) was treated as described in Example 1 to yield 0.9 g (90% ethyl) of 1-vinyl-6-fluoro-7-(4-methyl-1-piperazinyl)-4-oxo-1,4-dihydroquinoline-3-carboxylic acid. 242°–243° C.

EXAMPLE 10

A mixture of 1-ethyl-6-fluoro-7-chloro-4-oxo-1,4-dihydroquinoline-3-carboxylic acid ethyl ester (10 g), anhydrous piperazine (11.6 g) and 10 ml of 3-methoxybutanol was refluxed with stirring at 125° C. for 5 hrs. After cooling, 22 ml of 20% sodium hydroxide solution was added to the reaction mixture, and heated at 90° C. for 30 min. After cooling, 35 ml of water was added to the reaction mixture, the reaction mixture was adjusted to pH 7.5 with diluted acetic acid solution, appeared crystals were filtered. The crystals were dissolved in a solution of 42 ml of acetic acid in 52 ml of water, after treating with active carbon the solution was filtered, 4.5 ml of sulfuric acid was added to the filtrate. The appeared sulfuric acid salt was recrystallized from water. The obtained crystals were dissolved in a solution of 20% sodium hydroxide solution (9 ml) in 110 ml of water, and filtered. The filtrate was adjusted to pH 7.5, appeared crystals were washed with water.

These crystals were added to 100 ml of ethanol, and stirred for 1 hr, dried to give 9.2 g (85.8% yield, calculated from starting material) of 1-ethyl-6-fluoro-7-(1-piperazinyl)-4-oxo-1,4-dihydroquinoline-3-carboxylic acid. mp: 221°–222° C.

What is claimed is:

1. A process for the preparation of 1-substituted-6-fluoro-7-(1-piperazinyl or 4-substituted 1-piperazinyl)-4-oxo-1,4-dihydroquinoline-3-carboxylic acid having the structural formula (IV)

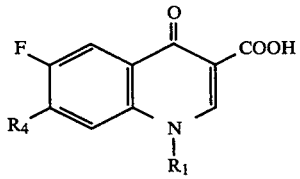

wherein $R_1$ and $R_2$ are defined as hereinafter, consisting essentially of reacting a 1-substituted-6-fluoro-7-chloro-4-oxo-1,4-dihydroquinoline-3-carboxylic acid ester derivative having the structural formula

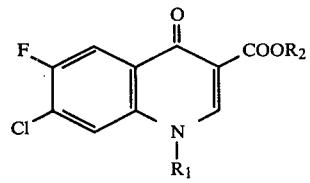

wherein $R_1$ is an ethyl or vinyl group, $R_2$ is a lower alkyl group, with a piperazine derivative having the structural formula (II)

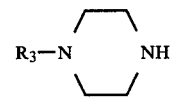

wherein $R_3$ is hydrogen atom or lower alkyl group, to produce a compound having the structural formula (III),

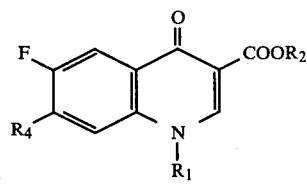

wherein $R_4$ is

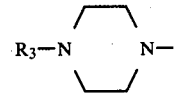

and $R_1$, $R_2$, and $R_3$ are defined as above, and then hydrolyzing the compound having structural formula (III).

* * * * *